United States Patent
Anastasio et al.

(10) Patent No.: US 11,403,792 B2
(45) Date of Patent: Aug. 2, 2022

(54) DEEP LEARNING-ASSISTED IMAGE RECONSTRUCTION FOR TOMOGRAPHIC IMAGING

(71) Applicant: WASHINGTON UNIVERSITY, St. Louis, MO (US)

(72) Inventors: Mark Anastasio, St. Louis, MO (US); Thomas Matthews, St. Louis, MO (US); Brendan Kelly, St. Louis, MO (US)

(73) Assignee: Washington University, St. Louis, MO (US)

( * ) Notice: Subject to any disclaimer, the term of this patent is extended or adjusted under 35 U.S.C. 154(b) by 293 days.

(21) Appl. No.: 16/616,742

(22) PCT Filed: Jun. 18, 2018

(86) PCT No.: PCT/US2018/038070
§ 371 (c)(1),
(2) Date: Nov. 25, 2019

(87) PCT Pub. No.: WO2018/236748
PCT Pub. Date: Dec. 27, 2018

(65) Prior Publication Data
US 2021/0150779 A1    May 20, 2021

Related U.S. Application Data

(60) Provisional application No. 62/521,670, filed on Jun. 19, 2017.

(51) Int. Cl.
*G06T 11/00*   (2006.01)
*G06N 20/00*   (2019.01)
(Continued)

(52) U.S. Cl.
CPC ............ *G06T 11/006* (2013.01); *A61B 5/055* (2013.01); *A61B 5/7264* (2013.01);
(Continued)

(58) Field of Classification Search
CPC ..... A61B 6/5205; A61B 5/7264; A61B 6/032; A61B 5/055; A61B 6/583; A61B 5/7267;
(Continued)

(56) References Cited

U.S. PATENT DOCUMENTS 4,984,160 A    1/1991   Felix et al.
5,576,548 A    11/1996  Clarke et al.
(Continued)

FOREIGN PATENT DOCUMENTS

EP    0749014 A1    12/1996
WO    2015140277 A1   9/2015
(Continued)

OTHER PUBLICATIONS

International Search Report for International Application No. PCT/US2018/038070, dated Nov. 8, 2018, 2 pages.
(Continued)

*Primary Examiner* — Brenda C Bernardi
(74) *Attorney, Agent, or Firm* — Armstrong Teasdale LLP

(57) ABSTRACT

Systems and methods for reconstructing an image of a subject or object based on a plurality of measured signals representing the subject or object obtained by an imaging device are disclosed. The systems and methods reconstruct the image of the subject or object by performing an iterative reconstruction method to produce a plurality of intermediate images and the image of the subject, and transforming at least one selected intermediate image from the plurality of intermediate images using a quasi-projection operator. The quasi-projection operator includes a deep-learning model configured to map the at least one selected intermediate
(Continued)

image to at least one regularized intermediate image. In addition, systems and methods for training the deep-learning model using a training data set that includes a plurality of training images and a plurality of corresponding training object images is disclosed.

25 Claims, 7 Drawing Sheets

(51) Int. Cl.
- *A61B 5/055* (2006.01)
- *A61B 5/00* (2006.01)
- *A61B 6/03* (2006.01)
- *A61B 6/00* (2006.01)

(52) U.S. Cl.
CPC ............ *A61B 5/7267* (2013.01); *A61B 6/032* (2013.01); *A61B 6/5205* (2013.01); *A61B 6/583* (2013.01); *G06N 20/00* (2019.01); *G06T 11/008* (2013.01); *G06T 2211/424* (2013.01)

(58) Field of Classification Search
CPC ...... G06N 20/00; G06N 3/0454; G06N 3/082; G06T 11/006; G06T 11/008; G06T 2211/424
See application file for complete search history.

(56) References Cited

U.S. PATENT DOCUMENTS

| | | | |
|---|---|---|---|
| 6,740,883 B1 | 5/2004 | Stodilka et al. | |
| 7,558,414 B2 | 7/2009 | Griswold | |
| 8,600,136 B2 | 12/2013 | Schweizer et al. | |
| 8,660,330 B2 | 2/2014 | Jarisch | |
| 8,917,268 B2 | 12/2014 | Johnsen et al. | |
| 8,992,405 B2 | 3/2015 | Chebrolu et al. | |
| 9,020,230 B2 | 4/2015 | Yu et al. | |
| 9,105,087 B2 | 8/2015 | Wang et al. | |
| 9,125,581 B2 | 9/2015 | Wu et al. | |
| 9,153,021 B2 | 10/2015 | Wilson | |
| 9,177,374 B2 | 11/2015 | Stayman et al. | |
| 9,189,871 B2 | 11/2015 | Pan et al. | |
| 9,486,142 B2 | 11/2016 | Hielscher et al. | |
| 9,524,567 B1 | 12/2016 | Brokish et al. | |
| 9,595,120 B2 | 3/2017 | Nguyen et al. | |
| 9,600,924 B2 | 3/2017 | Noo et al. | |
| 2012/0128265 A1 | 5/2012 | Silver | |
| 2014/0363067 A1 | 12/2014 | Stayman et al. | |
| 2015/0287223 A1 | 10/2015 | Bresler et al. | |
| 2015/0309136 A1 | 10/2015 | Shu et al. | |
| 2016/0242673 A1 | 8/2016 | Grychtol et al. | |
| 2016/0292589 A1 | 10/2016 | Taylor et al. | |
| 2016/0328643 A1 | 11/2016 | Liu et al. | |
| 2017/0186194 A1* | 6/2017 | Koehler | A61B 6/5282 |
| 2019/0325621 A1* | 10/2019 | Wang | A61B 6/037 |

FOREIGN PATENT DOCUMENTS

| | | |
|---|---|---|
| WO | 2016042466 A1 | 3/2016 |
| WO | 2016124395 A2 | 8/2016 |

OTHER PUBLICATIONS

Written Opinion of the International Search Authority for International Application No. PCT/US2018/038070, dated Nov. 8, 2018, 5 pages.

\* cited by examiner

DEEP LEARNING-ASSISTED IMAGE RECONSTRUCTION FOR TOMOGRAPHIC IMAGING

CROSS-REFERENCE TO RELATED APPLICATIONS

This application is a U.S. National Phase Application of PCT/US2018/038070, filed Jun. 18, 2018, which claims the benefit of priority to U.S. Provisional Patent Application Ser. No. 62/521,670, filed Jun. 19, 2017, the contents of which are hereby expressly incorporated by reference in their entirety.

BACKGROUND

Imaging techniques typically comprise detecting a plurality of image signals from a subject or object to be imaged and constructing an image based on the plurality of detected signals. The detected signals may be any detectable type of signal associated with the subject or object, including electromagnetic signals such as light, magnetic resonance signals, X-rays, acoustic signals such as ultrasound, ionization signals, and others. Existing imaging devices typically record a plurality of detected image signals and subsequently process the image signals using a reconstruction algorithm to form an image of the subject or object. These reconstructed images are typically formed from the detected image data using various mathematical and computational methods. Examples of imaging techniques that obtain images in this manner include, but are not limited to, computed tomography (CT), positron emission tomography (PET), single-photon emission computed tomography (SPECT), magnetic resonance imaging (MRI), electron paramagnetic resonance imaging (EPRI), wave imaging (such as phase contrast imaging, thermoacoustic imaging, photoacoustic imaging, and thermooptical imaging), and particle imaging.

In some cases, the plurality of image signals detected by the imaging device may be sufficient to produce an accurate and/or useful image by use of an image reconstruction method. However, in some situations, one may have access only to fractions of such measurements. Thus, in various forms of imaging, including tomography, a challenge in image reconstruction methodology centers on data sufficiency and on how to estimate an image, such as a tomographic image, when the projection data are not sufficient for reconstruction of an accurate and/or useful image.

In some cases, insufficient data result from inherent limitations associated with the imaging device and/or the limited scanning geometry of the imaging device. For example, the subject or object to be imaged may have a limited angular range accessible by the imaging device. By way of another example, gaps in the measured projection data may be caused by imaging hardware anomalies, such as bad detector bins, and/or by the presence of materials that may be incompatible with the imaging system, such as metal within the subject or object to be imaged. In other cases, the imaging system may acquire insufficient data by design, for example in order to reduce overall imaging time or exposure of the subject or object to ionizing radiation, laser energy, or other types of energy used by the imaging systems. Images reconstructed using standard analytic algorithms, such as filtered back-projection (FBP), may include conspicuous artifacts if the measured projection data are not sufficient for accurate reconstruction of tomographic images.

Existing alternative image reconstruction algorithms, such as iterative image reconstruction methods used in X-ray CT imaging, attempt to recover high-quality images from imperfect imaging data, such as data obtained using low-dose X-rays, incomplete imaging data, or limited imaging data. In addition, these existing alternative image reconstruction algorithms attempt to ameliorate the development of artifacts in the reconstructed images due to the presence of dense objects within the imaged volume, or the inclusion of imperfect models of the data acquisition process in the reconstruction algorithm. Existing iterative reconstruction methods typically incorporate detailed mathematical models of the image acquisition process, including models of the imaging system, noise, and images. These mathematical models are combined into an unconstrained or constrained optimization problem, which is then solved using an optimization algorithm.

The imaging models used in existing iterative reconstruction models describe the process of encoding properties of the subject or object to be imaged into a plurality of measured signals by the imaging device. In existing iterative reconstruction methods, the imaging model is typically incorporated within an objective function that is subject to one or more forms of regularization. These one or more forms of regularization penalize images that do not fit the prescribed model, or alternatively the regularization may constrain the solution to the objective function to contain the known properties of real-world images. In at least some iterative reconstruction methods, regularization represents one means by which a priori information characterizing the imaging system and/or the imaged subject or object may be introduced into the reconstruction process.

Iterative reconstruction methods typically include a process of sequentially reconstructing a plurality of intermediate images, with each intermediate image based at least in part on the preceding intermediate image, until a final image is produced. The final image represents the solution of an optimization problem within some predetermined tolerance selected by the user. In a typical iterative reconstruction method, an initial estimate of the image is first specified. From this initial image data, an imaging operator is used to generate synthetic tomographic data. The imaging operator mathematically represents, as closely as possible, the geometry of the imaging system and the data acquisition process and maps an estimated image to the corresponding tomographic data. The difference between the estimated tomographic data and the original measured tomographic data is then utilized to update the initial image to produce a subsequent intermediate image. The updated intermediate image may then be used to generate subsequent intermediate tomographic data in a subsequent iteration step with the aid of the imaging operator. The difference between the subsequent intermediate tomographic data and the original measurement signals is determined, and this difference is used to calculate an updated image, which in turn may be used to enhance the image data quality over the next iteration.

Choosing an appropriate regularization approach is a challenging aspect of existing iterative imaging reconstruction methods. In some existing methods, regularization is based on a fixed, analytic transformation that causes images to become sparse or approximately sparse in some transform domain, dictionary, or basis. For example, a total-variation regularization approach utilizes a finite-differencing matrix. As an additional example, regularization methods based on wavelet transformations have been used with limited success. However, existing regularization methods typically fail to fully capture the relevant details of the images. For example, total-variation regularization can result in images that include patchy artifacts as a result of assuming a simplistic model for the images. As a result, images produced using existing iterative reconstruction methods still include significant artifacts, limiting the usefulness of these iterative image reconstruction methods in clinical settings.

A need exists for improved image reconstruction methods that enhance the quality of images reconstructed from incomplete measurement data.

SUMMARY

In one aspect, a computer-implemented method for reconstructing an image of a subject based on a plurality of measured signals obtained by an imaging device is disclosed. The method includes performing, using a computing device, an iterative image reconstruction method to produce a plurality of intermediate images and to produce the image of the subject. The computer-implemented method also includes transforming, using the computing device, at least one selected intermediate image from the plurality of intermediate images using a quasi-projection operator. The quasi-projection operator includes a deep-learning model configured to map the at least one selected intermediate image to at least one regularized intermediate image.

In another aspect, a computer-implemented method for producing a quasi-projection operator that includes a deep learning model is disclosed. The quasi-projection operator is configured to regularize an intermediate image produced by an iterative image reconstruction method. The method includes training, using a computing device, a deep-learning model using a training data set. The training data set includes a plurality of training images and a plurality of corresponding training object images. Each corresponding training object image includes a representation of an object from which each training image is produced using the iterative reconstruction method. The deep-learning model is configured to map the intermediate image to a regularized intermediate image, and the iterative image reconstruction method is configured to reconstruct an image of a subject based on a plurality of measured signals obtained by an imaging device.

In an additional aspect, a computer system for reconstructing an image of a subject based on a plurality of measured signals obtained by an imaging device is disclosed. The computer system includes at least one processor in communication with at least one memory device. The at least one processor programmed to perform an iterative image reconstruction method to produce a plurality of intermediate images and to produce the image of the subject. The at least one processor is further programmed to transform at least one selected intermediate image from the plurality of intermediate images using a quasi-projection operator. The quasi-projection operator includes a deep-learning model configured to map the at least one selected intermediate image to at least one regularized intermediate image.

In another additional aspect, at least one non-transitory computer-readable storage media in communication with a computing device and having computer-executable instructions for reconstructing an image of a subject based on a plurality of measured signals obtained by an imaging device is described. When executed by at least one processor, the computer-executable instructions cause the at least one processor to perform an iterative image reconstruction method to produce a plurality of intermediate images and to produce the image of the subject. The computer-executable instructions further cause the at least one processor to transform at least one selected intermediate image from the plurality of intermediate images using a quasi-projection operator. The quasi-projection operator includes a deep-learning model configured to map the at least one selected intermediate image to at least one regularized intermediate image.

BRIEF DESCRIPTION OF THE DRAWINGS

The following figures illustrate various aspects of the disclosure.

Figure 1:
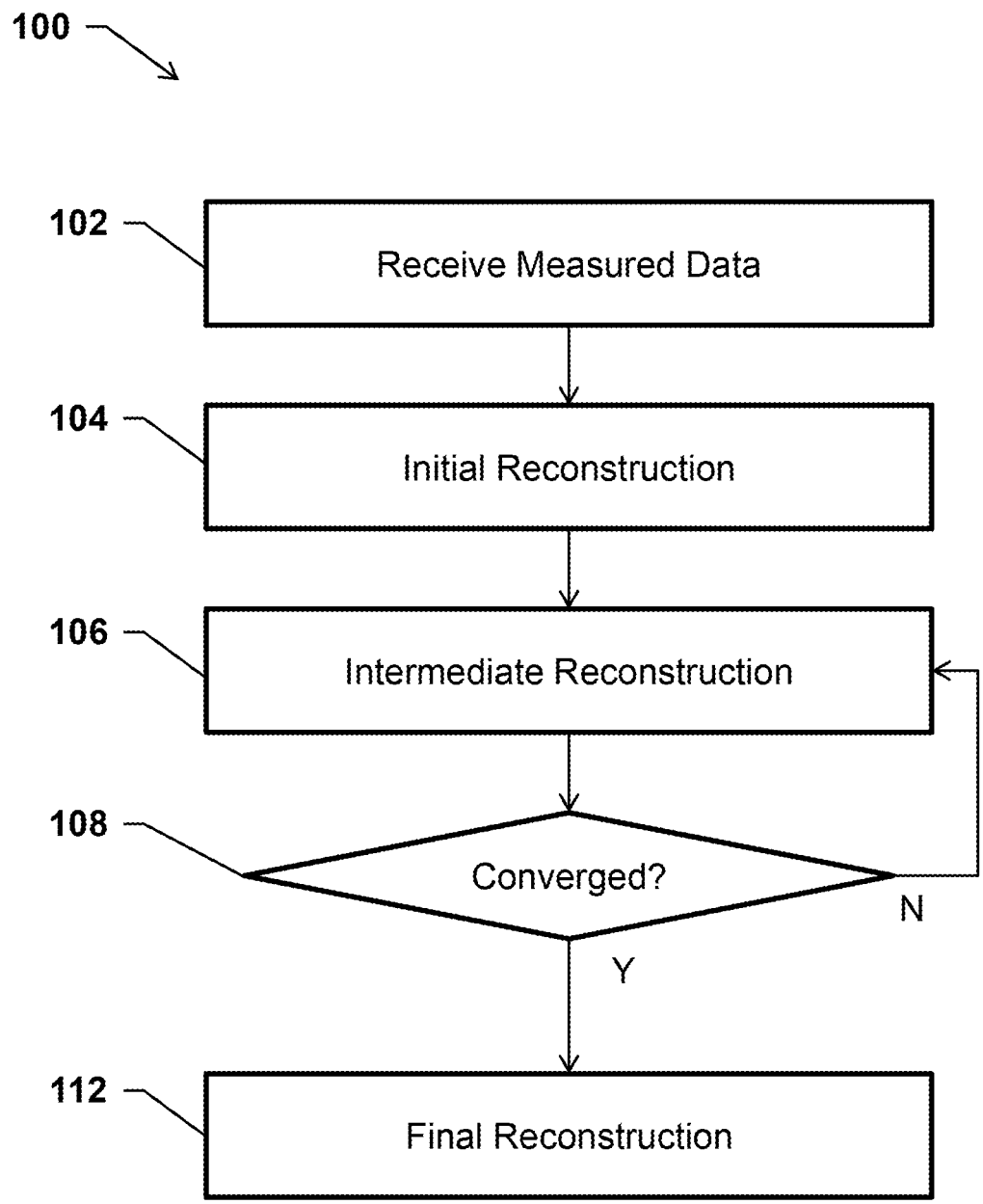
FIG. 1 is a block diagram illustrating an existing iterative image reconstruction method.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION

In various aspects, systems and computer-implemented methods for reconstructing an image of a subject or object based on a plurality of measured signals representing the subject or object obtained by an imaging device using a deep learning-assisted iterative reconstruction method are disclosed. The deep learning-assisted iterative reconstruction method includes the performance of regularization to an intermediate reconstructed image in the form of a quasi-projection (QP) operator based on a deep learning model invoked at least once during the image reconstruction process. The QP operator introduces a priori information captured by the deep learning model related to the subject or object to be imaged, the imaging system, and the iterative image reconstruction method that results in a reduction in artifacts and noise in the resulting image compared to a corresponding image reconstructed using the iterative image reconstruction method without regularization based on the QP operator.

The inclusion of regularization via the QP operator in the disclosed iterative image reconstruction methods represents a paradigm shift in the field of image reconstruction with potentially widespread applications to many forms of computed imaging beyond CT tomographic imaging as disclosed herein. The disclosed systems and computer-implemented methods enable accurate reconstruction of images from incomplete and/or noisy measurement data sets for a variety of imaging devices and reconstruction methods. In various aspects, the implementation of regularization using a deep learning-based QP operator is compatible for use with imaging data obtained using any known imaging device and data acquisition process. As a result, the disclosed deep learning-assisted iterative reconstruction methods are compatible with any imaging system and with any reconstruction algorithm for which sufficient training data may be obtained in various aspects.

In various aspects, the disclosed systems and methods enable accurate reconstruction of images using undersampled data sets obtained using magnetic resonance imaging (MRI) systems, thereby reducing data-acquisition time and enhancing the uses of MRI visualizations in a wide range of clinical applications. In other aspects, use of the disclosed systems and methods enable reductions of radiation doses used to obtain imaging data for X-ray computed tomography (CT). In additional aspects, the disclosed systems and methods enable the enhancement of the quality of images obtained by modern microscopy systems, including, but not limited to, electron tomography systems. In other additional aspects, the disclosed systems and methods are compatible with a wide range of non-biomedical applications of computed imaging.

In one aspect, for a typical imaging system in a discrete setting, the imaging system is described mathematically as Eqn. (1):

$$g = Hf;  \qquad \text{Eqn. (1)}$$

where the vector g represents the measured data, the vector f represents the sought-after object property, and the imaging operator H represents the action of the imaging system.

Without being limited to any particular theory, the image reconstruction problem generally entails determining an estimate of f that defines the image, for a given g (the measured tomographic data) and for a given H (a mathematical representation of the imaging system).

In this aspect, for an iterative image reconstruction method, the image reconstruction is formulated as an optimization problem, as expressed in Eqn. (2):

$$\hat{f} = \operatorname{argmin}_{f \in C} \{d(g, Hf) + R(f)\}; \qquad \text{Eqn. (2)}$$

where $\hat{f}$ represents a reconstructed image obtained as an estimate of the true object f, (d(g,HF)) represents losses associated with data fidelity, and R(f) represents losses associated with regularization.

In this aspect, the estimate of the reconstructed image $\hat{f}$ is formed by minimizing the objective function (d(g,HF)+R(f)) expressed as a sum of the losses associated with data fidelity and regularization, as specified on the right-hand side of Eqn. (2), subject to the constraint that the image is contained within the set C. Without being limited to any particular theory, the set C could be represented as the intersection of a collection of sets that represent different constraints on the image. The set C is typically defined to capture certain lower-level information about the class of objects to be imaged, effectively introducing a priori information regarding the object, imaging system, and or data acquisition process into the iterative reconstruction process. By way of non-limiting example, in some applications of the iterative image reconstruction method, the set C is defined to enforce non-negativity of the image estimate or to ensure that the components of $\hat{f}$ take on values within a pre-defined range.

In this aspect, the objective function (d(g,HF)+R(f)) in Eqn. (2) expresses the cost of the intermediate reconstructed image in the form of a real number. The term d(g,Hf) in Eqn. (2) is a function that represents the distance (or generalized distance) between the measured data g and the simulated tomographic data Hf that would be produced for a given ideal image f assuming idealized data acquisition and data processing by the imaging system as represented by the operator H. Because image reconstruction is generally an ill-conditioned problem, regularization is typically imposed to improve the quality of the reconstructed image estimate. This is accomplished by including the penalty term R(f) in Eqn. (2) to promote the formation of image estimates with desirable properties. In addition, regularization is further accomplished through the imposition of the constraint that the image estimate $\hat{f}$ must be contained in the set C. Without being limited to any particular theory, minimizing Eqn. (2) minimizes the generalized distance and shifts the reconstructed image (i.e. the image estimate $\hat{f}$) towards the original image.

In various aspects, a variety of methods are available for reconstructing images by approximately optimizing the objective function as expressed in Eqn. (2). Most methods are iterative in nature and involve use of a judiciously selected projection operator to enforce the constraint that the image estimate $\hat{f}$ must be contained in the set C ($\hat{f} \in C$). In one aspect, for a special case when the data fidelity and penalty terms in the objective function are differentiable, a projected gradient descent (P-GD) method is employed. The P-GD method is an iterative method in which, at each iteration, a gradient descent step and a projection onto the set C are applied to produce a subsequent intermediate image $f_{n+1}$ based on the previous intermediate image $f_n$. Let ($f_1$, $f_2$, ..., $f_n$) denote the intermediate image estimates of f produced by an iterative image reconstruction algorithm corresponding to different iterations. Using the P-GD method, the intermediate estimate of f for the $(n+1)^{th}$ iteration is given by Eqn. (3):

$$f_{n+1} = P_C(f_n - \alpha_n(\nabla_f d(g, Hf_n) + \nabla_f R(f_n))); \qquad \text{Eqn. (3)}$$

where $P_C$ represents the projection operator onto C, $\alpha_n$ represents the step size of each iterative step, and $\nabla_f$ is an operator denoting the gradient with respect to f. In an aspect, when the data fidelity term d(g, $Hf_n$) is differentiable but the penalty $R(f_n)$ is not, a proximal gradient method is employed.

FIG. 1 is a block diagram illustrating steps of an existing iterative image reconstruction method. The method 100 includes receiving the measured data obtained by an imaging device or imaging system at 102. The measured data received at 102 is utilized to produce an initial estimate of the image at 104. An intermediate image reconstruction step is performed at 106 based on either the initial estimated image obtained at 104 or an intermediate estimated image from a previous iteration of the image reconstruction method as described below. For example, the P-GD image reconstruction method may determine the intermediate image reconstruction at 106 using Eqn. (3) as described above. The intermediate image reconstructed at 106 is evaluated at 108 to determine whether there is convergence of the reconstructed image according to one or more predetermined convergence criteria. By way of non-limiting example, if a current image $f_{n+1}$ as calculated by Eqn. (3) differs from the previous image $f_n$ by more than a predetermined threshold difference, the current image $f_{n+1}$ is considered to be have not converged, and otherwise is considered to be have converged. If the current intermediate image is determined to have not converged at 108, another iteration of the image reconstruction method is performed at 106. If the current intermediate image reconstruction is determined to have converged at step 108, this estimated image is accepted as the final image at 112.

The inability to incorporate detailed a priori information about the class of objects to be imaged via the constraint f∈C limits the effectiveness of current image reconstruction methods, such as the P-GD described above and illustrated in FIG. 1. Ideally, the constraint set C would be defined in such a way that higher-level information about the class of objects to be imaged could be incorporated to improve the quality of the computed image estimate. For example, C could be defined to contain only image estimates that are free of artifacts and are not contaminated by high noise levels. By incorporating such information into the image reconstruction process, it would be possible to reconstruct accurate and/or sufficiently usable images from incomplete sets of noisy measurement data. Without being limited to any particular theory, an image reconstruction method that incorporates a priori information as described above would enable reductions of data-acquisition times and, for the case of X-ray imaging, reductions in radiation doses to the imaged patient.

In one aspect, higher-level information about the class of objects to be imaged is incorporated into the reconstruction process using a deep learning-assisted image reconstruction method. As used herein, deep learning (DL) refers to a sub-field of machine learning that uses many-layered Deep Neural Networks (DNNs) to learn levels of representation and abstraction that can be employed to extract information from or produce images. In this aspect, the deep learning-assisted image reconstruction is an extension of existing constrained optimization methods. In one aspect, the deep learning-assisted image reconstruction method involves introducing a new deep learning-assisted operator Q into the intermediate image reconstruction step as represented in Eqn. (3). The expression resulting from incorporating the deep learning-assisted operator Q, referred to herein as a quasi-projection (QP) operator, into Eqn. (3), is given by Eqn. (4):

$$f_{n+1} = Q(P_C(f_n - \alpha_n(\nabla_f d(g, Hf_n) + \nabla_f R(f_n)))); \qquad \text{Eqn. (4)}$$

In one aspect, the ordering in which the operators Q and $P_C$ are applied can be interchanged. In various aspects, the QP operator Q is configured to reduce the levels of artifacts and noise within at least one the intermediate image estimates produced using Eqn. (4) in place of Eqn. (3). Without being limited to any particular theory, the inclusion of the QP operator Q effectively guides the iterative reconstruction algorithm as expressed in Eqn. (4) to a more accurate final image estimate. In various aspects, the enhanced image accuracy enabled by the disclosed deep learning-assisted image reconstruction method is particularly effective when limited information (i.e. signals obtained by the imaging system) representing the object image to be reconstructed is available.

In an aspect, the QP operator Q is established by training a deep-learning (DL) model using a collection of representative images (simulated or experimentally-derived) and the corresponding reconstructed images produced at intermediate iterations of an optimization-based iterative reconstruction method as a training set. In one aspect, the collection of representative images is obtained by a suitable imaging device from an imaging phantom. The trained QP operator Q is configured to map an intermediate estimate of the image f, which contains artifacts and noise, to a benchmark image/object that contains reduced image artifacts and lower image noise levels and is representative of the collection of objects to be imaged.

In various aspects, the QP operator Q is established using any existing deep-learning (DL) methodology without limitation. The DL methodologies used to establish the QP operator Q include the use of any known network architecture without limitation. Non-limiting examples of suitable network architectures include fully convolutional networks characterized by a series of convolutional layers, autoencoder-style networks characterized by variable dimensionality of the network features that shrink and then expand during network optimization, and any other suitable network architecture without limitation. In one aspect, the network architecture replaces traditional convolution blocks with residual blocks to facilitate optimization in the disclosed deep learning-assisted image reconstruction methods.

In various other aspects, the deep-learning methodology may make use of any existing network training method without limitation. Non-limiting examples of suitable network training methods include: data augmentation, dropout, existing gradient descent optimization, and any other suitable network training method without limitation. Non-limiting examples of data augmentation include shifting, flipping, and/or cropping the training images to enable enhanced generalization of the convolutional neural network (CNN). Non-limiting examples of dropout includes randomly changing the network architecture during training by 'dropping out' selected nodes (i.e. deactivating or turning off). In various aspects, any suitable gradient descent optimizer may be selected to enable the gradient descent optimization of the convolutional neural network (CNN) including, but not limited to, ADAM, SGD, and RMSProp.

In one aspect, the QP operator Q is applied for at least one iteration of the iterative image reconstruction method, corresponding to the estimation of one intermediate image. In general, the iterative image reconstruction method includes producing a plurality of intermediate images according to optimization of an objective function including, but not limited to, the objective function in Eqn. (2) above. Each subsequent intermediate image is produced based on each preceding intermediate image according to the optimization of the objective function. In this aspect, for at least one intermediate image produced during one of the iterative steps, the intermediate image is transformed into a regularized intermediate image using the QP operator Q. In one aspect, the intermediate image is transformed into a regularized intermediate image using the QP operator Q by using Eqn. (4) in place of Eqn. (3) to determine the intermediate image $f_{n+1}$. Without being limited to any particular theory, the regularized intermediate image is characterized by reduced artifacts and noise, relative to an intermediate image produced without regularization, by virtue of the information encoded by the deep-learning process within the QP operator Q. In this aspect, the regularized intermediate image calculated using Eqn. (4) replaces the intermediate image ordinarily calculated using Eqn. (3) for this iterative step and is used in the place of the intermediate image to produce the subsequent intermediate image calculated using Eqn. (3) according to optimization of the objective function without regularization performed for the remaining intermediate image reconstruction steps.

In various other aspects, the QP operator Q is applied to an iterative image reconstruction method at multiple selected intermediate images associated with multiple iterations according to a regularization schedule including, but not limited to, a predetermined regularization schedule, an adaptively determined regularization schedule, and/or any other suitable regularization schedule. In some aspects, the QP operator Q is applied at after a predetermined number of iterations of an iterative image reconstruction method have occurred. In some aspects, the QP operator Q is applied at after a fixed number of iterations including, but not limited to, 2 iterations, 5 iterations, 10 iterations, 20 iterations, 25 iterations, 30 iterations, 40 iterations, 50 iterations, 60 iterations, 70 iterations, 75 iterations, 80 iterations, 90 iterations, 100 iterations, or greater than 100 iterations have occurred since the last application of the QP operator Q. In another aspect, if the number of iterations to be used by the iterative image reconstruction method is known, the QP operator Q may be applied at uniform intervals throughout the total number of iterations of the iterative image reconstruction method. In this other aspect, the number of uniform intervals is 2, 4, 6, 8, 10, 20, 25, 50, 75, 100, or 100 more uniform intervals. In various additional aspects, the interval at which the QP operator Q is applied may be dynamically determined according to an adaptive scheme. In one additional aspect, the QP operator Q is applied when a predetermined loss level, as quantified by a value of the objective function corresponding to an intermediate image, falls below a threshold objective function value during the iterative image reconstruction method.

In various aspects, the QP operator Q is applied to one intermediate image within an iterative image reconstruction method at least one time after the one intermediate image has been determined to converge according to one or more criteria in accordance with the iterative image reconstruction method. Without being limited to any particular theory, the criteria used to determine the convergence of a reconstructed image incorporate criteria including, but not limited to, expressions indicating changes in the reconstructed image relative to a previous iteration of the reconstructed image, expressions indicating a computational cost including, but not limited to, processing time, and any other suitable criterion. Non-limiting examples of criteria used to define convergence of a reconstructed image include a total number of image reconstruction iterations in excess of a threshold maximum number of iterations, a relative change between intermediate images falling below a convergence threshold value, a computational cost exceeding a maximum threshold computational cost, and a minimum Euclidean or $l^2$ norm of the gradient $\nabla_f$.

Figure 2:
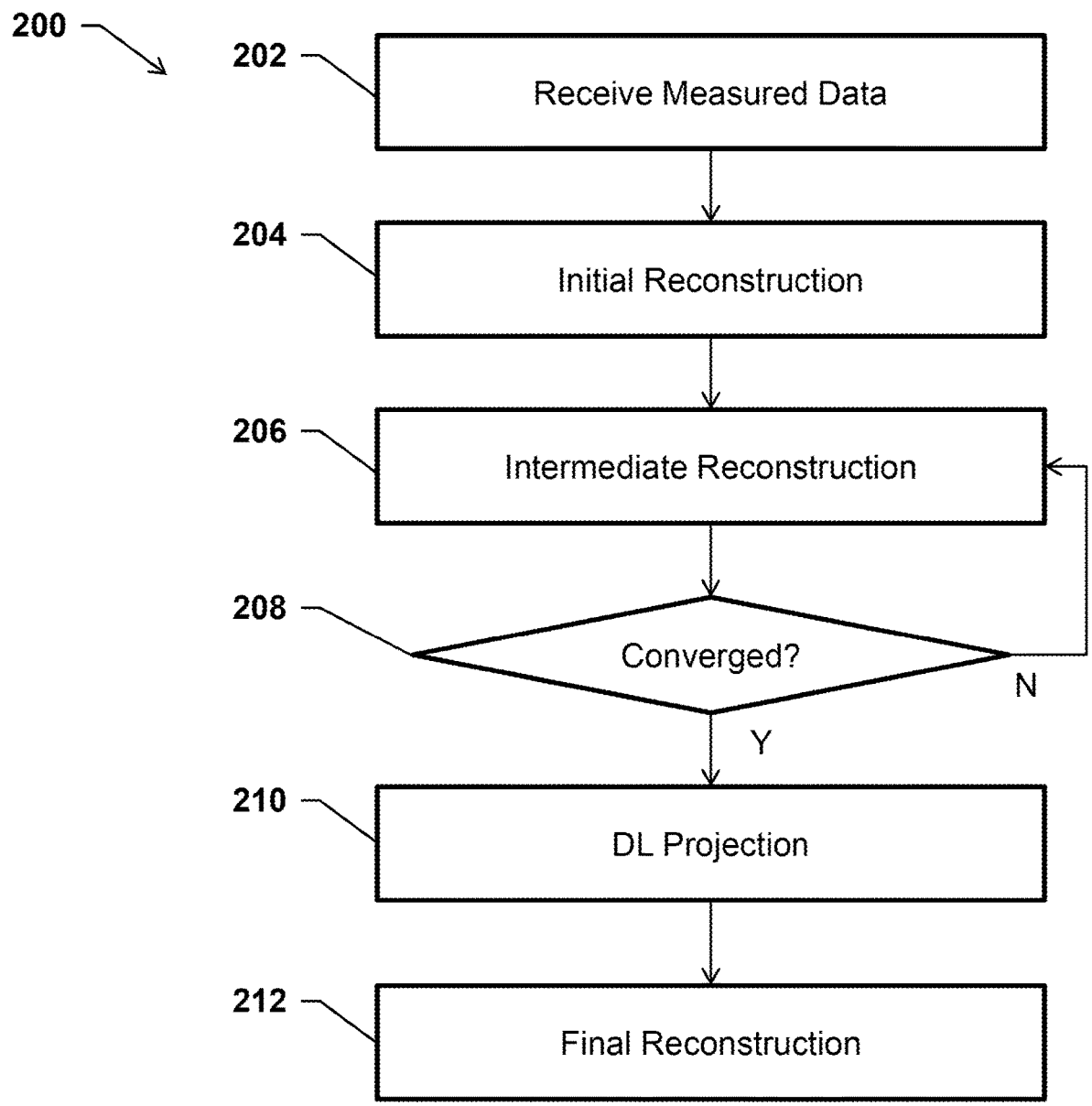
FIG. 2 is a block diagram illustrating a deep learning-assisted image reconstruction method according to one aspect of the disclosure.

FIG. 2 is a block diagram illustrating one deep learning-assisted iterative image reconstruction method in one aspect. In this aspect, the deep learning projection (i.e., the QP operator Q) is performed after convergence of an intermediate image reconstruction to enhance the quality of the final reconstructed image. The method 200 includes receiving the measured imaging data obtained by an imaging device or imaging system at 202. The measured data received at 202 is employed to obtain an initial estimate of the image at 204. An intermediate image reconstruction step is performed at 206 based on either the initial estimated image obtained at 204 or an intermediate reconstructed image obtained from a previous iteration as described below. The intermediate image reconstructed at 206 is evaluated at 208 to determine whether there is convergence of the reconstructed image according to the one or more criteria as described above. If the current intermediate image is determined to have not converged at 208, another iteration of intermediate image reconstruction is performed at 206. If the current intermediate image reconstruction is determined to have converged at step 208, a deep learning projection is performed based on the current intermediate image at 210 and the resulting projection is used to reconstruct the final image at 212. By way of non-limiting example, deep learning projection may be enabled using the QP operator Q as described above and applied at 210 in one aspect.

Figure 3:
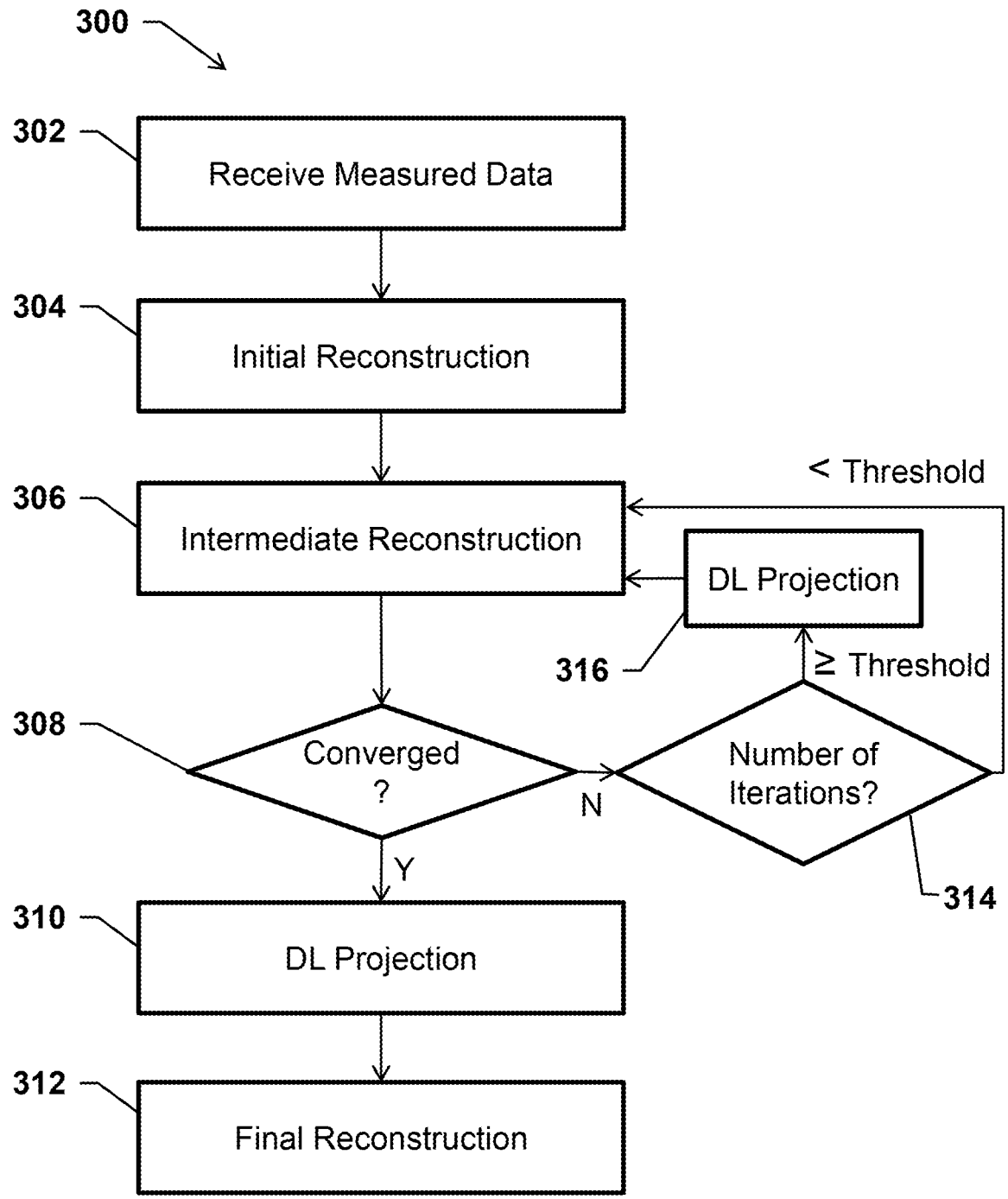
FIG. 3 is a block diagram illustrating a deep learning-assisted image reconstruction method according to a second aspect of the disclosure.

FIG. 3 is a block diagram illustrating a deep learning-assisted iterative image reconstruction method in another aspect. In this other aspect, the deep learning projection is performed multiple times to enable at least one or more enhancements of an existing iterative image reconstruction method including, but not limited to, accelerating the convergence of the intermediate reconstructed images and enhancing the quality of the final reconstructed image. As illustrated in FIG. 3, the method 300 includes receiving the measured data obtained by an imaging device or imaging system at 302. The measured data received at 302 is utilized to obtain an initial estimate of the image at 304. One or more intermediate image reconstruction steps are performed at 306 based on either the estimated initial image obtained at 304 or from an intermediate reconstructed image from a previous iteration as described below. The intermediate image reconstructed at 306 is evaluated at 308 to determine whether there is convergence of the reconstructed image according to the one or more criteria as described above. If the current intermediate image is determined to have not converged at 308, other criteria may be evaluated to determine whether to perform another iteration of intermediate image reconstruction at 306 or whether to perform a DL projection at 316 prior to performing another iteration of image reconstruction at 304. As illustrated in FIG. 3, the current number of iterations of the image reconstruction method may be compared to a threshold number of iterations at 314. In this aspect, the threshold number of iterations of intermediate image reconstruction defines an interval at which the deep-learning projection of the intermediate image is invoked at 316. If the current intermediate image reconstruction is determined to have converged at step 308, a deep learning projection is optionally performed based on the current intermediate image at 310 and a final image is obtained at 312 based on the DL projection performed at 310. By way of non-limiting example, the DL projection is enabled in the form of the QP operator Q as described above and applied at 310 and 316 in one aspect.

In various other aspects, the QP operator Q is applied at every iteration of an iterative image reconstruction method. By way of non-limiting example, the QP operator Q is introduced in the P-GD method described and summarized in Eqn. (4) above, effectively applying the QP operator Q at every iteration of the P-GD method.

Without being limited to any particular theory, by modulating the rate at which the QP operator Q is applied in an iterative image reconstruction method, the influence of the learned higher-level information about the class of objects on the final reconstructed object estimate is varied. The introduction of this learned higher-level information via the QP operator Q provides a means by which the reconstruction method can be responsive to information in the measured data that is not reflected in the training data that is employed to establish the QP operator Q. The number of times the QP operator Q is applied during an image reconstruction in the deep learning-assisted iterative image reconstruction method may be modulated in a manner analogous to the modulation of weighting terms on total variation penalties invoked in some existing iterative image reconstruction methods.

Without being limited to any particular theory, because the QP operator Q inherently includes a priori information related to the object and/or the imaging system, the suitability of the QP operator Q is highest for those applications most similar to the training dataset. In various aspects, a different QP operator Q is provided for each particular type of imaging device and/or image reconstruction method used to produce the image of a subject or object. In some aspects, different QP operators are produced for use with different types of imaging devices (CT scanner versus MRI scanner), different models of the same type of imaging device (3T MRI scanner versus 7T MRI scanner), different individual scanners of the same type and model, and the same imaging device after different cumulative hours of use. In other aspects, different QP operators are produced for use with different standard poses of the subject or object used to obtain images using an imaging device. By way of non-limiting example, different QPs may be used for different parts of the subject or object (head versus hip) and for different poses of the same part of the subject or object (lateral view versus dorsal-ventral view). In various other aspects, different QPs may be used for the same imaging device and same pose of the same part of a subject or object, but at different iterations during the iterative image reconstruction method ($100^{th}$ iteration versus $1000^{th}$ iteration of reconstruction using an iterative reconstruction method). In other additional aspects, the disclosed method includes at least two or more of the different QPs described above in any combination without limitation.

In one aspect, the QP operator Q is established using the training data set as described above starting from a naïve or untrained initial state. In another aspect, the QP operator Q is produced using the training data set but starting with an existing QP operator Q. In some aspects, the existing QP operator Q is trained using a previous training data set similar in any one or more factors to the current training data set including, but not limited to: same type of imaging device, same model of imaging device, same part of subject or object, same pose of same part of subject or object, and any combination thereof. In another aspect, the QP operator Q associated with a particular imaging system is dynamically updated using training data obtained from each subsequent image produced by the imaging device.

In various aspects, the deep learning-assisted image reconstruction method includes utilizing a suitable iterative image reconstruction algorithm to reduce the corresponding objective function values associated with the intermediate images subject to certain constraints as described above. At certain iterations in the algorithm, the QP operator Q is applied to the current intermediate estimated image of the object as described above. In one aspect, the iterative image reconstruction algorithm with periodic applications of the QP operator Q is continued until a convergence condition is satisfied.

Although the deep learning-assisted image reconstruction method is disclosed herein in terms of iterative image reconstruction methods related to CT image reconstruction, the deep-learning derived QP operator Q is compatible with a wide variety of imaging devices and image reconstruction methods, so long as a training database is available containing high-quality images that contain no or minimal image artifacts and zero or low image noise levels. The deep-learning derived QP operator Q is compatible with any image reconstruction method including, but not limited to, non-iterative (one-shot) reconstruction methods and iterative image reconstruction methods. In some aspects, including, but not limited to, image reconstruction methods that do not include an initial estimate of the image, the QP operator Q is used to accelerate the convergence of the final image with little effect on image quality.

Figure 4:
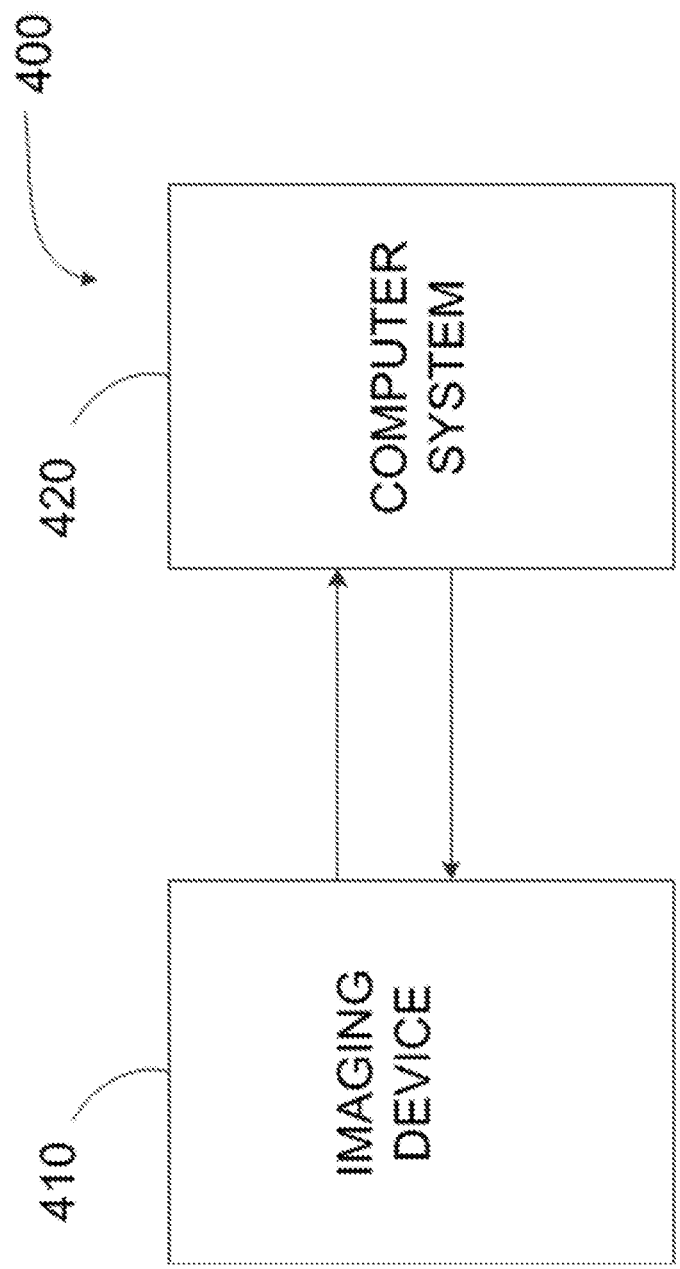
FIG. 4 is a schematic block diagram of an imaging system according to one aspect of the disclosure.

In various aspects, the methods described herein may be implemented using an imaging system. FIG. 4 is an illustration of an imaging system 400 in one aspect. As illustrated in FIG. 4, the imaging system 400 may include an imaging device 410 operatively coupled and/or in communication with a computer system 420. In this aspect, the computer system 420 is configured to receive data including, but not limited to, a plurality of measured signals representing the imaged subject or object, a plurality of parameters defining the image reconstruction method, and a plurality of parameters representing at least one QP operator Q. The computer system 420 is further configured to execute a plurality of stored executable instructions encoding one or more aspects of the disclosed method as described herein above. In another aspect, the computer system 420 may be further configured to operate the imaging device 410 to obtain the plurality of measured signals representing the imaged subject or object that are received by the computer system 420, thereby enabling the disclosed methods by executing an additional plurality of stored executable instructions.

Although the disclosed systems and methods are described in connection with an imaging system 400, the disclosed systems and methods are operational with numerous other general purpose or special purpose imaging system environments or configurations. The imaging system environment is not intended to suggest any limitation as to the scope of use or functionality of any aspect of the disclosed systems and methods. Moreover, the imaging system environment should not be interpreted as having any dependency or requirement relating to any one or combination of components illustrated in the exemplary operating environment. Examples of well-known imaging systems, environments, and/or configurations that may be suitable for use with aspects of the invention include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like. By way of non-limiting example, embodiments of the invention are operational in a cloud computing environment such that the computer system 420 receives data from one or more computers (not shown) within the imaging system 400 or remote from the imaging system 400.

Computer systems, as described herein, refer to any known computing device and computer system. As described herein, all such computer systems include a processor and a memory. However, any processor in a computer system referred to herein may also refer to one or more processors wherein the processor may be in one computing device or a plurality of computing devices acting in parallel. Additionally, any memory in a computer device referred to herein may also refer to one or more memories wherein the memories may be in one computing device or a plurality of computing devices acting in parallel.

The term processor, as used herein, refers to central processing units, microprocessors, microcontrollers, reduced instruction set circuits (RISC), application specific integrated circuits (ASIC), logic circuits, and any other circuit or processor capable of executing the functions described herein. The above are examples only, and are thus not intended to limit in any way the definition and/or meaning of the term "processor."

As used herein, the term "database" may refer to either a body of data, a relational database management system (RDBMS), or to both. As used herein, a database may include any collection of data including hierarchical databases, relational databases, flat file databases, object-relational databases, object oriented databases, and any other structured collection of records or data that is stored in a computer system. The above examples are example only, and thus are not intended to limit in any way the definition and/or meaning of the term database. Examples of RDBMS's include, but are not limited to including, Oracle® Database, MySQL, IBM® DB2, Microsoft® SQL Server, Sybase®, and PostgreSQL. However, any database may be used that enables the systems and methods described herein. (Oracle is a registered trademark of Oracle Corporation, Redwood Shores, Calif.; IBM is a registered trademark of International Business Machines Corporation, Armonk, N.Y.; Microsoft is a registered trademark of Microsoft Corporation, Redmond, Wash.; and Sybase is a registered trademark of Sybase, Dublin, Calif.)

In one embodiment, a computer program is provided to enable the image reconstruction method as described herein above, and this program is embodied on a computer readable medium. In an example embodiment, the computer system is executed on a single computer system, without requiring a connection to a server computer. In a further embodiment, the computer system is run in a Windows® environment (Windows is a registered trademark of Microsoft Corporation, Redmond, Wash.). In yet another embodiment, the computer system is run on a mainframe environment and a UNIX® server environment (UNIX is a registered trademark of X/Open Company Limited located in Reading, Berkshire, United Kingdom). Alternatively, the computer system is run in any suitable operating system environment. The computer program is flexible and designed to run in various different environments without compromising any major functionality. In some embodiments, the computer system includes multiple components distributed among a plurality of computing devices. One or more components may be in the form of computer-executable instructions embodied in a computer-readable medium.

The computer systems and processes are not limited to the specific embodiments described herein. In addition, components of each computer system and each process can be practiced independent and separate from other components and processes described herein. Each component and process also can be used in combination with other assembly packages and processes.

Figure 5:
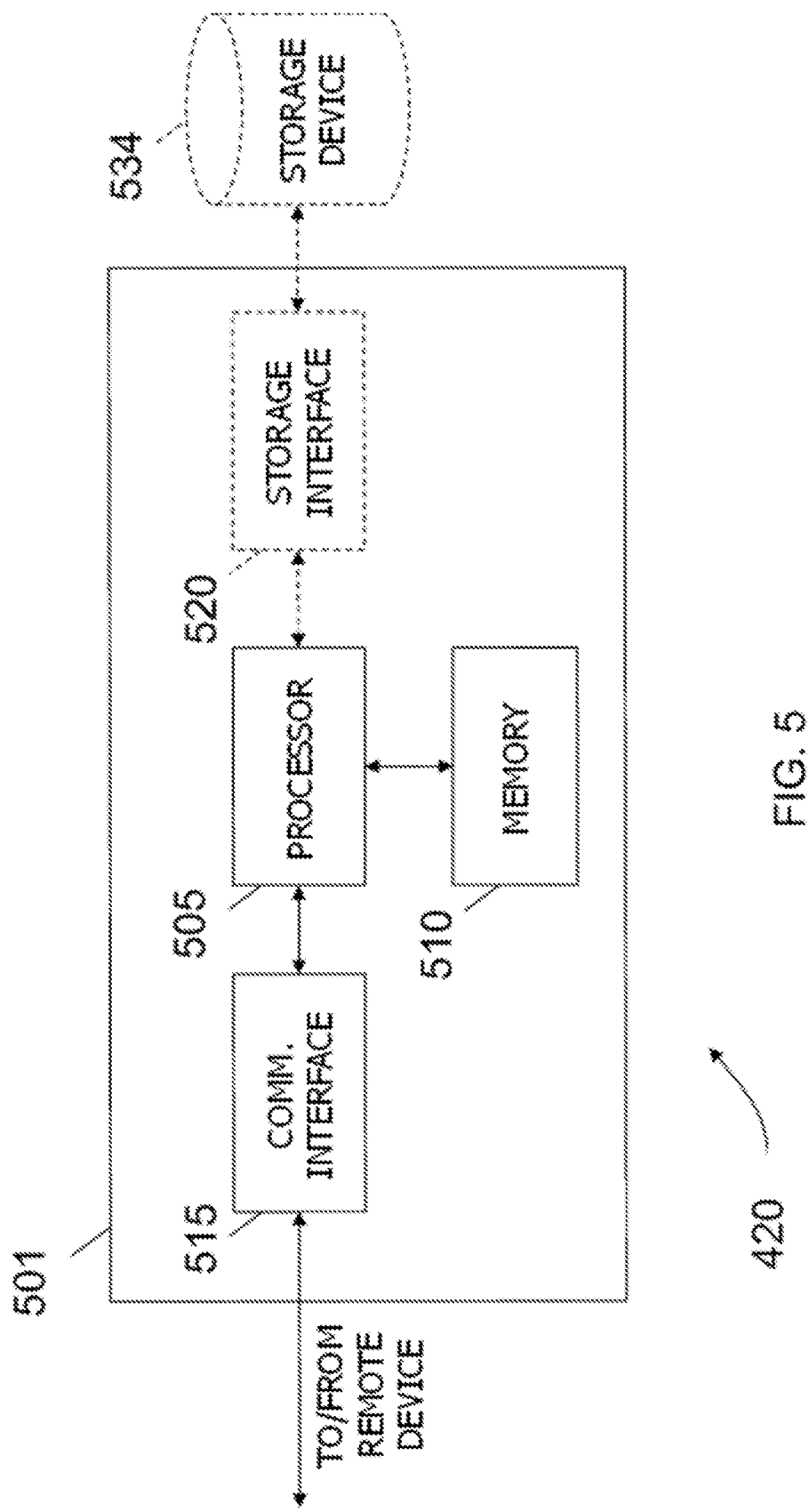
FIG. 5 is a schematic block diagram of an example server system according to one aspect of the disclosure.

In one embodiment, the computer system 420 may be configured as a server system. FIG. 5 illustrates an example configuration of a server system 501 used to receive measured signals received from the subject or object to be reconstructed into an image representing the subject or object. Referring again to FIG. 5, server system 501 may also include, but is not limited to, a database server. In this example embodiment, server system 501 performs all of the steps used to implement the image reconstruction method as described herein above.

In this aspect, the server system 501 includes a processor 505 for executing instructions. Instructions may be stored in a memory area 510, for example. The processor 505 may include one or more processing units (e.g., in a multi-core configuration) for executing instructions. The instructions may be executed within a variety of different operating systems on the server system 501, such as UNIX, LINUX, Microsoft Windows®, etc. It should also be appreciated that upon initiation of a computer-based method, various instructions may be executed during initialization. Some operations may be required in order to perform one or more processes described herein, while other operations may be more general and/or specific to a particular programming language (e.g., C, C#, C++, Java, or any other suitable programming languages).

The processor 505 is operatively coupled to a communication interface 515 such that server system 501 is capable of communicating with a remote device, such as the imaging device 410 (see FIG. 4), a user system, or another server system 501. For example, communication interface 515 may receive requests (e.g., requests to provide an interactive user interface to receive sensor inputs and to control one or more devices of imaging system 400 from a client system via the Internet.

Processor 505 may also be operatively coupled to a storage device 534. Storage device 534 is any computer-operated hardware suitable for storing and/or retrieving data. In some embodiments, storage device 534 is integrated in server system 501. For example, server system 501 may include one or more hard disk drives as storage device 534. In other embodiments, storage device 534 is external to server system 501 and may be accessed by a plurality of server systems 501. For example, storage device 534 may include multiple storage units such as hard disks or solid state disks in a redundant array of inexpensive disks (RAID) configuration. Storage device 534 may include a storage area network (SAN) and/or a network attached storage (NAS) system.

In some embodiments, processor 505 is operatively coupled to storage device 534 via a storage interface 520. Storage interface 520 is any component capable of providing processor 505 with access to storage device 534. Storage interface 520 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 505 with access to storage device 534.

Memory area 510 may include, but are not limited to, random access memory (RAM) such as dynamic RAM (DRAM) or static RAM (SRAM), read-only memory (ROM), erasable programmable read-only memory (EPROM), electrically erasable programmable read-only memory (EEPROM), non-volatile RAM (NVRAM), registers, hard disk memory, a removable disk, a CD-ROM, or any other form of computer-readable storage medium known in the art. The above memory types are exemplary only, and are thus not limiting as to the types of memory usable for storage of a computer program.

Figure 6:
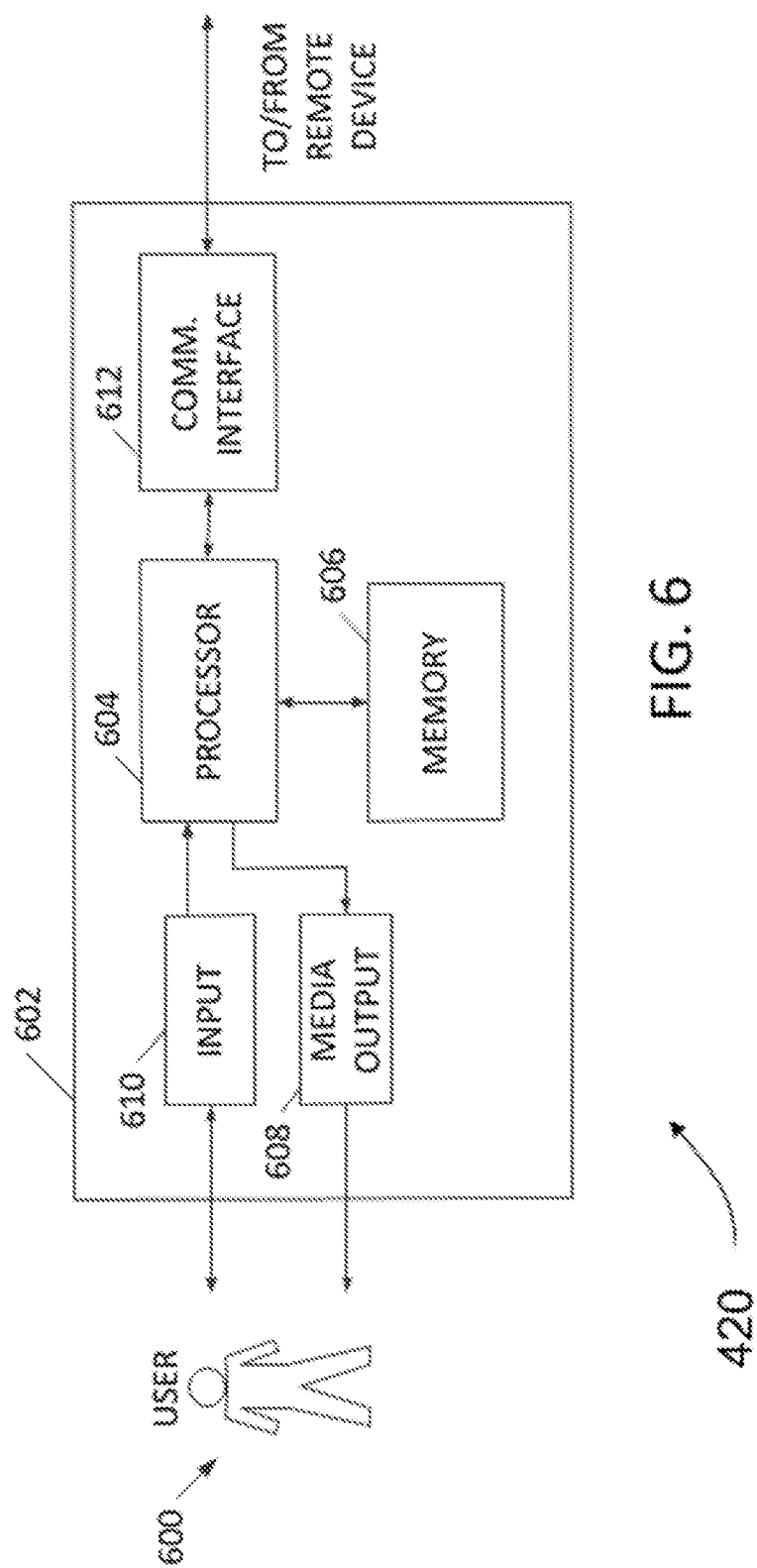
FIG. 6 is a block diagram of an example computing device according to one aspect of the disclosure.

In another embodiment, the computer system 420 may be provided in the form of a computing device, such as a computing device 602 as illustrated in FIG. 6. Computing device 602 includes a processor 604 for executing instructions. In some embodiments, executable instructions are stored in a memory area 606. Processor 604 may include one or more processing units (e.g., in a multi-core configuration). Memory area 606 is any device allowing information such as executable instructions and/or other data to be stored and retrieved. Memory area 606 may include one or more computer-readable media.

In another embodiment, the memory included in the computing device 602 may include a plurality of modules (not shown). Each module may include instructions configured to execute using at least one processor 604. The instructions contained in the plurality of modules may implement at least part of the disclosed image reconstruction method by regulating a plurality of process parameters as described herein when executed by the one or more processors 604 of the computing device. Non-limiting examples of modules stored in the memory 606 of the computing device 602 include: a first module to receive measurements from one or more sensors and a second module to control one or more devices of the imaging system 400.

Computing device 602 also includes one media output component 608 for presenting information to a user 600. Media output component 608 is any component capable of conveying information to user 600. In some embodiments, media output component 608 includes an output adapter such as a video adapter and/or an audio adapter. An output adapter is operatively coupled to processor 604 and is further configured to be operatively coupled to an output device such as a display device (e.g., a liquid crystal display (LCD), organic light emitting diode (OLED) display, cathode ray tube (CRT), or "electronic ink" display) or an audio output device (e.g., a speaker or headphones).

In some embodiments, client computing device 602 includes an input device 610 for receiving input from user 600. Input device 610 may include, for example, a keyboard, a pointing device, a mouse, a stylus, a touch sensitive panel (e.g., a touch pad or a touch screen), a camera, a gyroscope, an accelerometer, a position detector, and/or an audio input device. A single component such as a touch screen may function as both an output device of media output component 608 and input device 610.

Computing device 602 may also include a communication interface 612, which is configured to communicatively couple to a remote device such as server system 501 or a web server. Communication interface 612 may include, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WIMAX)).

Stored in memory 606 is, for example, computer-readable instructions for providing a user interface to user 600 via media output component 608 and, optionally, receiving and processing input from input device 610. A user interface may include, among other possibilities, a web browser and an application. Web browsers enable users 600 to display and interact with media and other information typically embedded on a web page or a website from a web server. An application allows users 600 to interact with a server application.

EXAMPLE

The following example illustrates various aspects of the disclosure.

Figure 7A:
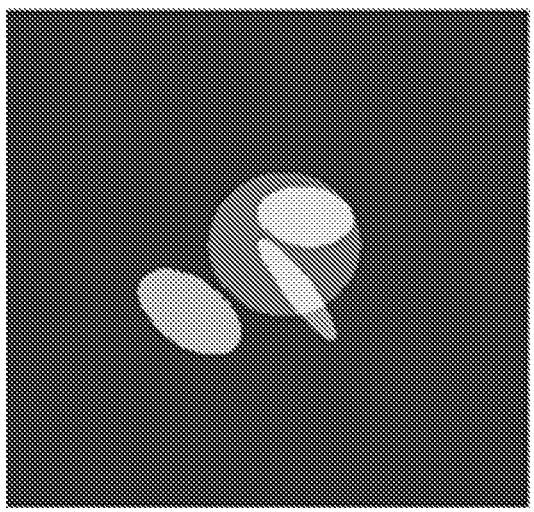
FIG. 7A is an image of a true object used as a reference for a computer-simulation study of deep-learning assisted image reconstructing according to one aspect of the disclosure.
Figure 7B:
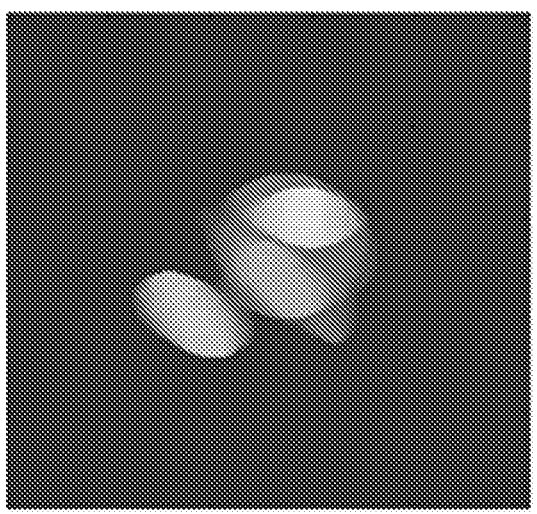
FIG. 7B is an estimated image of the object shown in FIG. 1A produced by reconstructing simulated CT imaging data using an existing image reconstruction method.
Figure 7C:
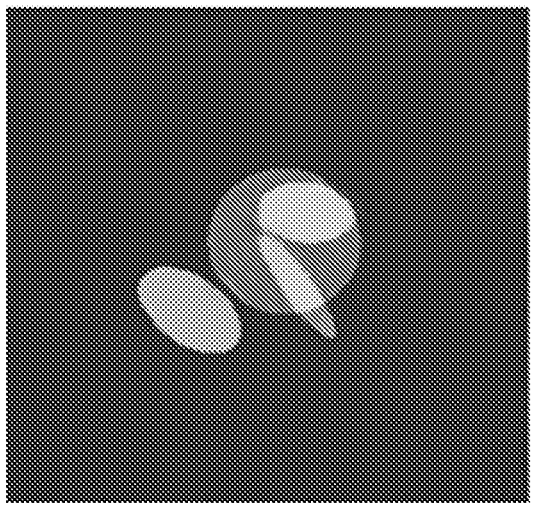
FIG. 7C is an estimated image of the object shown in FIG. 1A produced by reconstructing simulated CT imaging data using a deep-learning (DL) assisted image reconstruction method according to one aspect of the disclosure.

Example 1: Computer-Simulated Deep Learning-Assisted Image Reconstruction Assessment Computer-simulation studies were conducted to demonstrate the effectiveness of the deep learning-assisted image reconstruction method as described above. Simulated tomographic projection data were computed corresponding to a parallel-beam X-ray CT or to a radially-sampled MRI system. Sixty tomographic projections that spanned an angular range of 60 degrees were computed for each case. The simulated data acquisition protocol corresponded to a severely under-sampled test case in which conventional image reconstruction approaches would not be expected to perform well. From a collection of simulated objects, a deep learning model was trained to form the quasi-projection (QP) operator. Images were reconstructed by use of a gradient-based method in which the QP operator Q was applied at a specified subset of iterations. The set C was defined as the set of all non-negative images. No additional regularization was employed. Images were also reconstructed for the case where C was defined as the set of all non-negative images and R(f) was the total-variation seminorm. FIG. 7A is the true image of the object used to perform the computer-simulated study. FIG. 7B and FIG. 7C contain the images reconstructed using an existing image reconstruction method (FIG. 7B) and the deep-learning assisted image reconstruction method (FIG. 7C) described above. The image reconstructed using the deep-learning assisted image reconstruction method (FIG. 7C) was much more accurate than the image reconstructed using the existing image reconstruction method (FIG. 7B), demonstrating that the disclosed method can dramatically outperform existing state-of-the art image reconstruction methods.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A computer-implemented method for reconstructing an image of a subject based on a plurality of measured signals obtained by an imaging device, the method comprising:
    performing, using a computing device, an iterative image reconstruction method to produce a plurality of intermediate images and to produce the image of the subject; and
    transforming, using the computing device, at least one selected intermediate image from the plurality of intermediate images using a quasi-projection operator, the quasi-projection operator comprising a deep-learning model configured to map the at least one selected intermediate image to at least one regularized intermediate image,
    wherein transforming the at least one selected intermediate image further comprises selecting, using the computing device, each selected intermediate image according to a predetermined regularization schedule, and wherein selecting each selected intermediate image according to the predetermined regularization schedule comprises selecting, using the computing device, each selected intermediate image following production of a preselected number of intermediate images, wherein each selected intermediate image is separated from each adjacent selected intermediate image by the preselected number of intermediate images.

2. The computer-implemented method according to claim 1, wherein each regularized intermediate image comprises less image artifacts and lower image noise relative to each corresponding selected intermediate image.

3. The computer-implemented method according to claim 1, wherein performing the iterative image reconstruction method further comprises:

calculating, using the computing device, a corresponding objective function value for each intermediate image, the corresponding objective function value comprising a sum of losses associated with data fidelity and regularization; and projecting, using the computing device, each subsequent intermediate image based on each intermediate image and the corresponding objective function value using a projection operator, the projection operator further configured to optimize the corresponding objective function value.

4. The computer-implemented method according to claim 1, further comprising training, using the computing device, the deep-learning model using a training data set, the training data set comprising a plurality of training images and a corresponding plurality of training object images, and each training object image comprising a representation of an object from which each training image is produced using the iterative image reconstruction method.

5. The computer-implemented method according to claim 4, further comprising obtaining, using the computing device, the training data set using a simulation of the imaging device.

6. The computer-implemented method according to claim 4, further comprising obtaining, using the computing device, the training data set using imaging data obtained by the imaging device from an imaging phantom.

7. The computer-implemented method according to claim 3, wherein transforming the at least one selected intermediate image of the iterative image reconstruction method further comprises selecting, using the computing device, each selected intermediate image according to an adaptively determined regularization schedule.

8. The computer-implemented method according to claim 7, wherein selecting each selected intermediate image according to the adaptively determined regularization schedule comprises selecting, using the computing device, each selected intermediate image when the corresponding objective function value is less than a threshold objective function value.

9. The computer-implemented method according to claim 1, wherein performing the iterative image reconstruction method to produce the image of the subject further comprises:

identifying, using the computing device, one intermediate image of the plurality of intermediate images as converged if a difference between the one intermediate image and a preceding intermediate image is less than a convergence threshold or if a computational cost associated with performing the iterative image reconstruction method exceeds a maximum threshold computational cost; and transforming, using the computing device, the one intermediate image using the quasi-projection operator to produce the image of the subject.

10. A computer-implemented method for producing a quasi-projection operator comprising a deep learning model, the quasi-projection operator configured to regularize an intermediate image produced by an iterative image reconstruction method, the method comprising:

training, using a computing device, the deep-learning model using a training data set, the training data set comprising a plurality of training images and a plurality of corresponding training object images, each corresponding training object image comprising a representation of an object from which each training image is produced using the iterative image reconstruction method, wherein:

the deep-learning model is configured to map the intermediate image to a regularized intermediate image; and the iterative image reconstruction method is configured to reconstruct an image of a subject based on a plurality of measured signals obtained by an imaging device, wherein the training data set is obtained using a simulation of the imaging device.

11. The computer-implemented method according to claim 10, wherein the training data set is obtained by the imaging device from an imaging phantom.

12. A system for reconstructing an image of a subject based on a plurality of measured signals obtained by an imaging device, the system including at least one processor in communication with at least one memory device, the at least one processor programmed to:

perform an iterative image reconstruction method to produce a plurality of intermediate images and to produce the image of the subject; and transform at least one selected intermediate image from the plurality of intermediate images using a quasi-projection operator, the quasi-projection operator comprising a deep-learning model configured to map the at least one selected intermediate image to at least one regularized intermediate image, wherein the at least one processor is further programmed to select each selected intermediate image according to a predetermined regularization schedule, and wherein the at least one processor is further programmed to select each selected intermediate image following production of a preselected number of intermediate images, wherein each selected intermediate image is separated from each adjacent selected intermediate image by the preselected number of intermediate images.

13. The system according to claim 12, wherein each regularized intermediate image comprises less image artifacts and lower image noise relative to each corresponding selected intermediate image.

14. The system according to claim 12, wherein the at least one processor is further programmed to:

calculate a corresponding objective function value for each intermediate image, the corresponding objective function value comprising a sum of losses associated with data fidelity and regularization; and project each subsequent intermediate image based on each intermediate image and the corresponding objective function value using a projection operator, the projection operator further configured to optimize the corresponding objective function value.

15. The system according to claim 12, wherein the at least one processor is further programmed to train the deep-learning model using a training data set, the training data set comprising a plurality of training images and a plurality of corresponding training object images, and each corresponding training object image comprising a representation of an object from which each training image is produced using the iterative image reconstruction method.

16. The system according to claim 15, wherein the at least one processor is further programmed to obtain the training data set using a simulation of the imaging device.

17. The system according to claim 15, wherein the at least one processor is further programmed to obtain the training data set using imaging data obtained by the imaging device from an imaging phantom.

18. The system according to claim 12, wherein the at least one processor is further programmed to select each selected intermediate image according to an adaptively determined regularization schedule.

19. The system according to claim 14, wherein the at least one processor is further programmed to select each selected intermediate image when the corresponding objective function value is less than a threshold objective function value.

20. The system according to claim 12, wherein the at least one processor is further programmed to:
identify one intermediate image of the plurality of intermediate images as converged if a difference between the one intermediate image and a preceding intermediate image is less than a convergence threshold or if a computational cost associated with performing the iterative image reconstruction method exceeds a maximum threshold computational cost; and
transform the one intermediate image using the quasi-projection operator to produce the image of the subject.

21. At least one non-transitory computer-readable storage media in communication with a computing device and having computer-executable instructions for reconstructing an image of a subject based on a plurality of measured signals obtained by an imaging device, wherein when executed by at least one processor, the computer-executable instructions cause the at least one processor to:
perform an iterative image reconstruction method to produce a plurality of intermediate images and to produce the image of the subject; and
transform at least one selected intermediate image from the plurality of intermediate images using a quasi-projection operator, the quasi-projection operator comprising a deep-learning model configured to map the at least one selected intermediate image to at least one regularized intermediate image,
wherein the computer-executable instructions further cause the at least one processor to select each selected intermediate image following production of a preselected number of intermediate images, wherein each selected intermediate image is separated from each adjacent selected intermediate image by the preselected number of intermediate images.

22. The computer-readable media of claim 21, wherein the computer-executable instructions further cause the at least one processor to:
calculate a corresponding objective function value for each intermediate image, the corresponding objective function value comprising a sum of losses associated with data fidelity and regularization; and
project each subsequent intermediate image based on each intermediate image and the corresponding objective function value using a projection operator, the projection operator further configured to optimize the corresponding objective function value.

23. The computer-readable media of claim 21, wherein the computer-executable instructions further cause the at least one processor to train the deep-learning model using a training data set, the training data set comprising a plurality of training images and a plurality of corresponding training object images, and each corresponding training object image comprising a representation of an object from which each training image is produced using the iterative image reconstruction method.

24. The computer-readable media of claim 22, wherein the computer-executable instructions further cause the at least one processor to select each selected intermediate image when the corresponding objective function value is less than a threshold objective function value.

25. The computer-readable media of claim 21, wherein the computer-executable instructions further cause the at least one processor to:
identify one intermediate image of the plurality of intermediate images as converged if a difference between the one intermediate image and a preceding intermediate image is less than a convergence threshold or if a computational cost associated with performing the iterative image reconstruction method exceeds a maximum threshold computational cost; and
transform the one intermediate image using the quasi-projection operator to produce the image of the subject.

* * * * *